United States Patent [19]

Saadat

[11] Patent Number: 5,746,737
[45] Date of Patent: May 5, 1998

[54] ENCLOSURE FOR A LASING DEVICE

[75] Inventor: Vahid Saadat, Irvine, Calif.

[73] Assignee: Trimedyne, Inc., Irvine, Calif.

[21] Appl. No.: 485,362

[22] Filed: Jun. 7, 1995

[51] Int. Cl.[6] .................................................. A61B 17/36
[52] U.S. Cl. ........................... 606/15; 606/16; 607/89
[58] Field of Search ........................ 606/2, 7, 8, 13–15, 606/17, 18, 28, 33; 607/88–90, 92

[56] References Cited

U.S. PATENT DOCUMENTS

| | | | |
|---|---|---|---|
| 4,445,892 | 5/1984 | Hussein et al. | 604/101 |
| 4,539,987 | 9/1985 | Nath et al. | 128/303.1 |
| 4,672,961 | 6/1987 | Davies | 128/303.1 |
| 4,693,556 | 9/1987 | McCaughan | 350/320 |
| 4,740,047 | 4/1988 | Abe et al. | 350/96.15 |
| 4,782,818 | 11/1988 | Mori | 128/6 |
| 4,842,390 | 6/1989 | Sottini et al. | 350/96.15 |
| 4,844,580 | 7/1989 | Lynch et al. | 350/96.18 |
| 4,848,339 | 7/1989 | Rink et al. | 128/303.1 |
| 5,032,123 | 7/1991 | Katz et al. | 606/15 |
| 5,320,620 | 6/1994 | Long et al. | 606/2 |
| 5,495,541 | 2/1996 | Murray et al. | 606/17 |
| 5,496,307 | 3/1996 | Daikuzono | 606/7 |
| 5,496,309 | 3/1996 | Saadat et al. | 606/15 |
| 5,509,917 | 4/1996 | Cecchetti et al. | 606/14 |
| 5,562,658 | 10/1996 | Long | 606/15 |

*Primary Examiner*—Jennifer Bahr
*Assistant Examiner*—Bryan K. Yarnell
*Attorney, Agent, or Firm*—Olson & Hierl, Ltd.

[57] ABSTRACT

An attachable enclosure for a lateral lasing device comprising a fiber optic for emitting a laser beam and an exposed reflector for laterally reflecting the laser beam opposite the distal end of the fiber optic. The enclosure comprises an elongated body having a head portion with an open end and a tail portion. The elongated body defines a longitudinal flute for receiving and immobilizing the mounting stem of the lateral lasing device within its body. The hollow envelope has an open end and a fluid exit port, and is removably mounted to the head portion of the elongated body at its open end. The hollow envelope is dimensioned to surround the laser beam reflector and is in fluid flow communication with the longitudinal flute through the open end of the hollow envelope.

32 Claims, 5 Drawing Sheets

ENCLOSURE FOR A LASING DEVICE

FIELD OF THE INVENTION

The present invention relates to an attachable or exchangeable enclosure for a laser device used in medical procedures, which enclosure protects the laser device and also permits the laser device to be adapted for different medical procedures.

BACKGROUND OF THE INVENTION

Laser devices for use in various types of surgery are known. Such devices cause thermal coagulation and/or ablation of tissue by emission of a predetermined level of laser energy for a predetermined time. Lateral lasing devices for use in surgery include means for directing the laser beam laterally so as to impact tissue that is not in direct line with the fiber optic that delivers the laser beam. Usually, a lateral lasing device utilizes an endoscope or like viewing device to position the laser beam at a desired site for performing a medical procedure, such as for example prostatic surgery. One such lateral lasing device has a metal tip at its distal end provided with a reflective surface that directs a laser beam laterally, and is described in U.S. Pat. No. 5,242,437 to Everett et al.

The unwanted tissue can be coagulated to the desired depth or ablated by subjecting the tissue to laser energy. As coagulated tissues expand due to localized edema, heated blood and other fluid is driven ahead of the coagulation zone, producing a hyperemic ring and coagulative necrosis of tissue extending beyond the coagulated area. As a result, thermal necrosis and ultimate absorption or dissolution of the unwanted material can be achieved over a period of time, without bleeding. The device can also be used in near contact or contact mode with the coagulated tissue to ablate the same, thereby offsetting some or all of the swelling due to edema and enabling earlier voiding of urine by the patient.

As with virtually all lasing devices, the tip of the above-described lasing device frequently comes in contact with body tissue during surgery either accidently during the coagulation procedure or as part of an ablation procedure. Such contact tends to damage the tip, as tissue may adhere thereto, leaving heavy residue which may reduce the energy output and possibly cause the tip to melt due to localized overheating. Further, even if no tissue contact is made, blood and the debris tend to accumulate onto the tip due to back-splatter, which may cover and possibly damage the reflective surface.

Therefore, it is an object of this invention to provide an attachable device for enclosing the tip of a lateral lasing device so as to protect the tip from contact with body tissue and fluids while the desired medical procedure is performed.

It is a further object of the present invention to provide such a device that can be quickly and easily assembled onto the lateral lasing device.

It is a further object of the present invention to provide a channel and outlet for fluid flow to cool and clean the reflective surface of the lateral lasing device, with a means to orient said fluid flow in a desired direction with respect to the reflective surface.

It is a still further object of the present invention to provide such a device that can be used in thermal coagulation procedures and, if desired, in ablation procedures.

It is a still further object of the present invention to provide such a device that includes indicia for use in assembling the enclosure onto the lateral lasing device as well as indicia that indicate to the surgeon the direction of the laser beam.

SUMMARY OF THE INVENTION

In accordance with these and other objects of the invention, an attachable enclosure is provided for a lateral lasing device having a fiber optic with a distal end adapted for emitting a laser beam onto an exposed lateral reflector for the laser beam.

The attachable enclosure comprises an elongated body and a hollow envelope mounted to the elongated body, sized to receive therewithin the lateral reflector. The elongated body has a head portion and a tail portion with an open end. The elongated body defines a longitudinal flute for receiving a mounting stem of the lasing device within the body.

The mounting stem is immobilized within the flute in any suitable manner. For example, a coil spring may be seated within a circumferential groove defined on the inner side of the head portion for exerting an immobilizing force on the mounting stem. Alternatively, the head portion and the mounting stem may be sized or configured in a manner such that the head portion exerts an immobilizing force on the mounting stem.

The hollow envelope, at least a portion of which in the preferred embodiment is transparent to the wavelength of light being utilized, is made from a material such as quartz, fused silica or synthetic sapphire, and has an open end and a fluid exit port opposite the open end. The envelope is removably mounted to the head portion at its open end. The hollow envelope is dimensioned to surround the laser beam reflector and is in fluid flow communication with the longitudinal flute through the open end of the elongated body.

The enclosure in accordance with the present invention can be attachable or exchangeable, and protects the tip of the lateral lasing device from exposure to tissue and body fluids during surgery, thereby avoiding the problems associated with exposing the tip therefrom during surgery. The enclosure can be quickly and easily assembled onto the lateral lasing device, removed and readily replaced thereafter as required. The overall contour of the enclosure can vary to facilitate a desired medical procedure, e.g., coagulation, ablation, cutting, and the like. In addition, the enclosure enables the lasing device to be used for thermal coagulation as well as ablation procedures without risk of damaging the tip of the lasing device, inasmuch as a cooling liquid can be circulated through the enclosure while the lateral lasing device is in use. Further, if desired, indicia can be provided on the enclosure for use in assembling the enclosure onto the lateral lasing device and for indicating to the surgeon the direction of the emitted laser beam.

BRIEF DESCRIPTION OF THE DRAWINGS

The present invention and the advantages thereof will become more apparent upon consideration of the following detailed description when taken in conjunction with the accompanying drawings in which.

3

Figure 4:
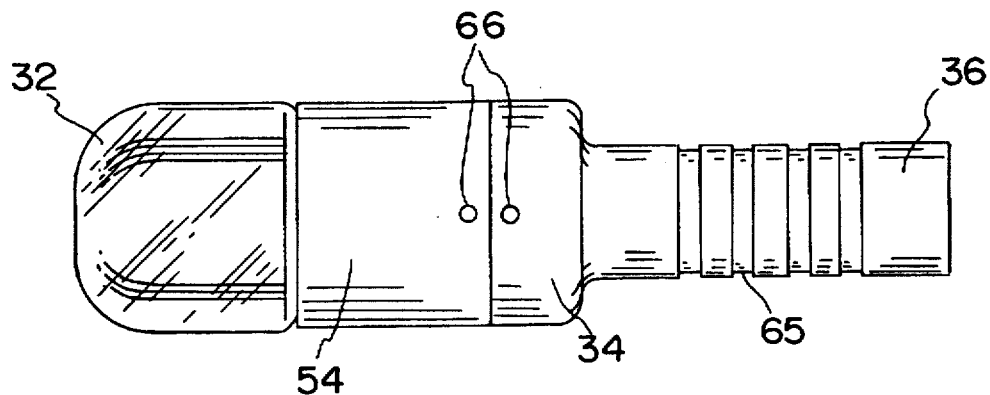
Figure 5:
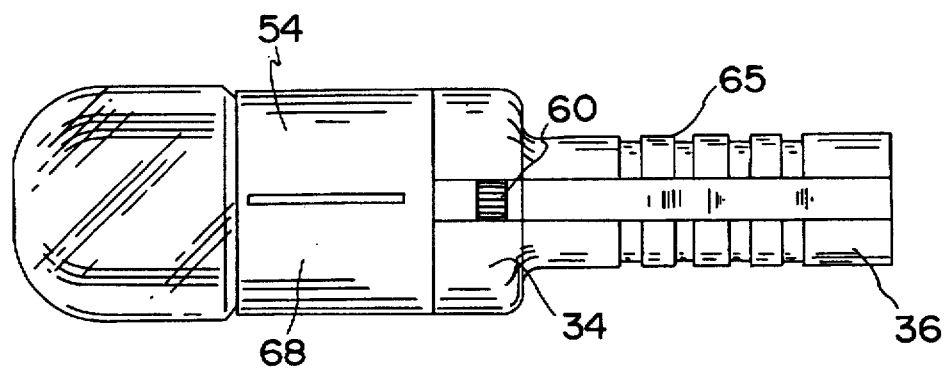
Figure 6:
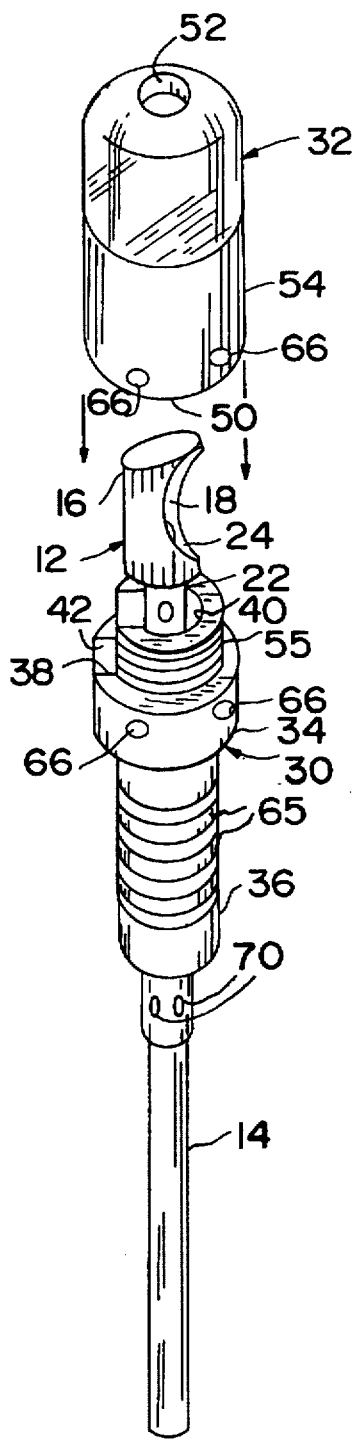
Figure 7:
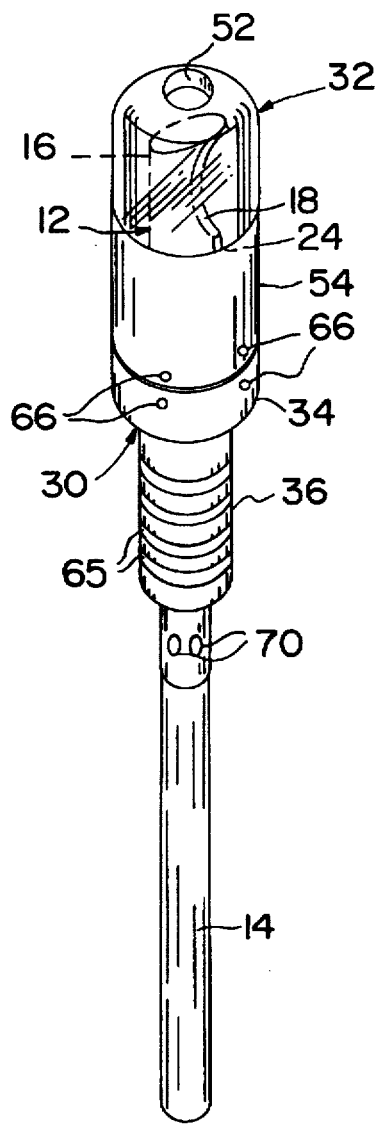
Figure 8:
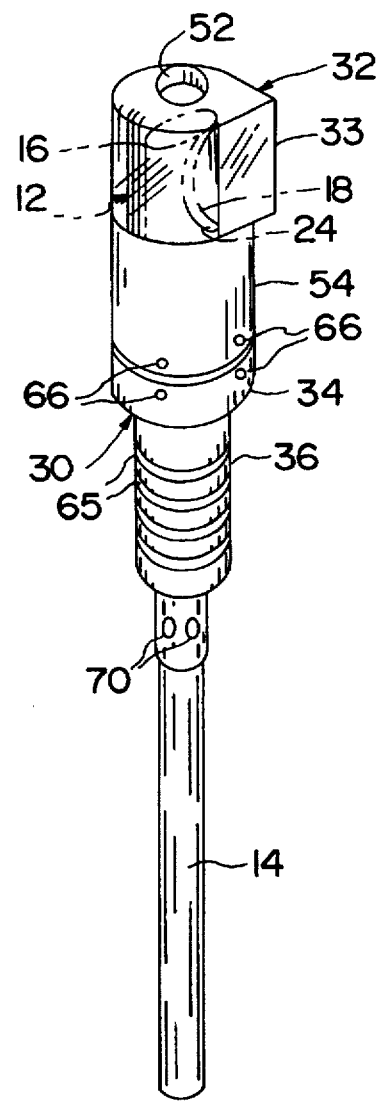
Figure 9:
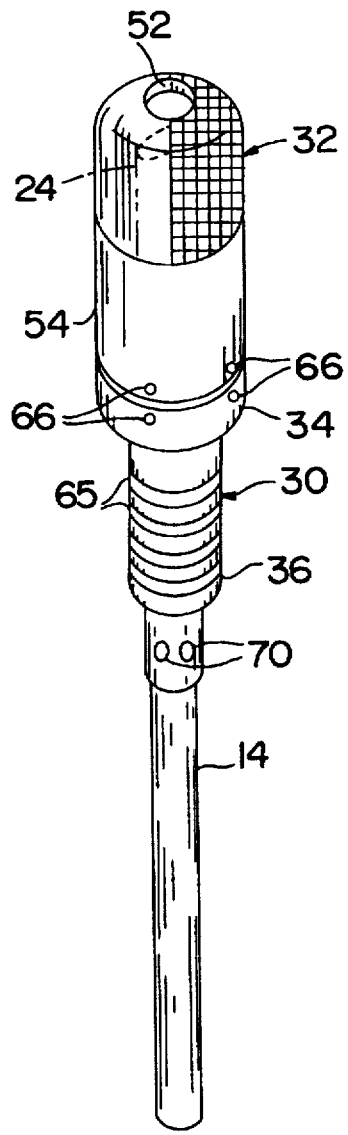
Figure 10:
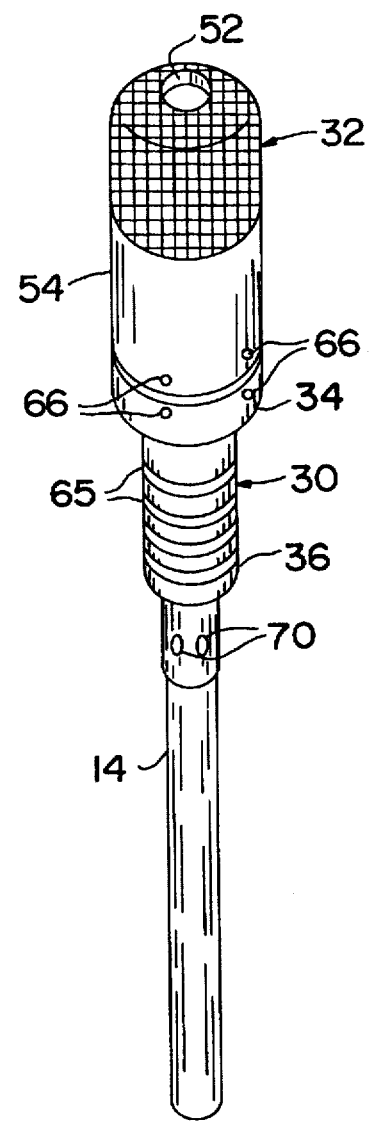

FIG. 4 is a plan view of one side of an enclosure in accordance with an alternative embodiment of the invention and having an indicator for aligning the head and tail portions of the enclosure;

FIG. 5 is a plan view of the other side of the enclosure of FIG. 4, illustrating an indicator for revealing the firing direction of the lateral lasing device;

FIG. 6 is an exploded, perspective view of an enclosure in accordance with another embodiment of the invention and a lateral lasing device;

FIG. 7 is a perspective view of the enclosure and lasing device of FIG. 6 secured together;

FIG. 8 is a perspective view of another embodiment of the present invention, illustrating an enclosure having a lateral cutting edge;

FIG. 9 is a perspective view of another embodiment of the invention, illustrating the enclosure partially coated with (or partially constructed of) an opaque material; and FIG. 10 is a perspective view of another embodiment of the invention, illustrating the enclosure coated with (or constructed of) an opaque material.

DETAILED DESCRIPTION OF THE PREFERRED EMBODIMENTS

Figure 1:
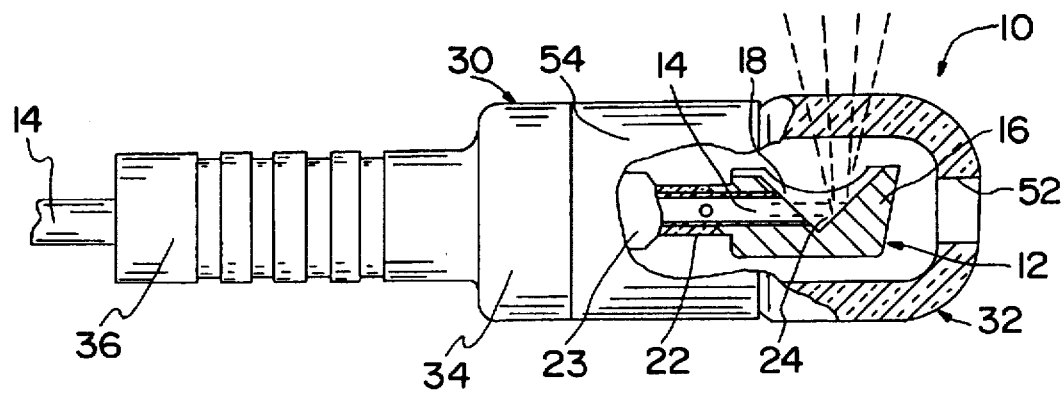
FIG. 1 is an elevation view, partially broken away to show interior detail, of an enclosure in accordance with a preferred embodiment of the invention shown secured to a lateral lasing device.

Referring to FIG. 1, an attachable or exchangeable enclosure 10 in accordance with the present invention is shown secured to a lateral lasing device 12. The lasing device illustrated in FIG. 1 is a lateral-lasing fiber optic apparatus that comprises a fiber optic 14 and a metal tip 16 defining a reflective cavity 18. A mounting stem 22, which preferably is integral with the metal tip 16, secures the metal tip to the fiber optic 14 and contains a somewhat larger diameter segment 23 that functions as a heat sink. The reflective cavity 18 provides a curved surface that defines a lateral reflector 24 for directing outwardly the energy emitted from the distal end of fiber optic 14.

Figure 2:
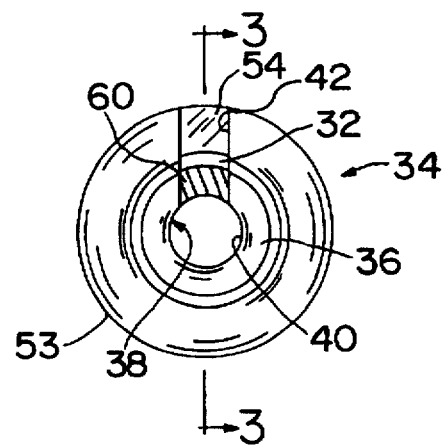
FIG. 2 is a proximal end view of the enclosure of FIG. 1 partially coated with an opaque material.
Figure 3:
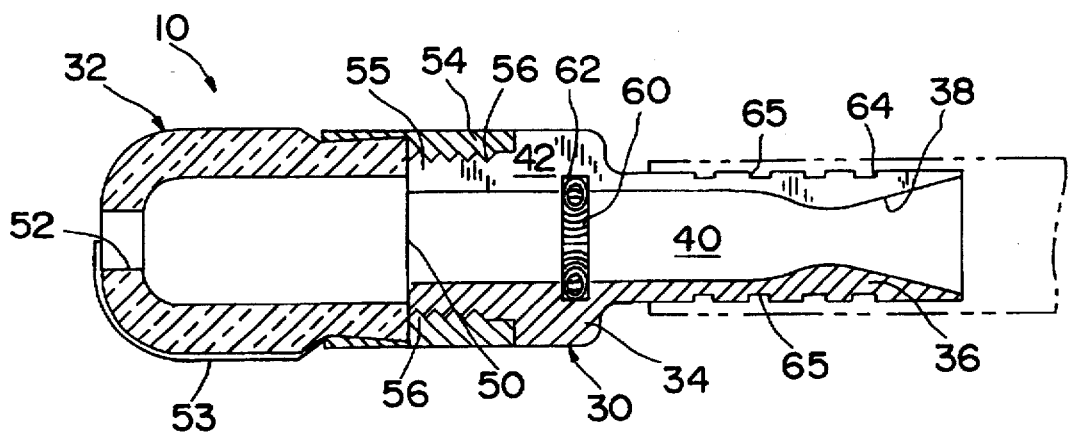
FIG. 3 is a section view taken along the plane 3—3 of FIG. 2, illustrating with dashed lines an irrigation tube for supplying a cooling liquid during medical procedures.

In a preferred embodiment, shown in FIGS. 2 and 3, the attachable enclosure 10 generally comprises an elongated body 30 and a hollow envelope 32 mounted thereto. The elongated body 30 comprises a head portion 34 and a unitary tail portion 36. A longitudinal bore or flute 38, for receiving the mounting stem 22 within the elongated body 30, is defined within the elongated body 30. The flute 38 includes a cylindrical bore 40, which is sized to receive the heat sink segment 23 of mounted stem 22, and a longitudinal groove 42 that intersect and together extend along the length of the elongated body 30. Accordingly, the transverse cross section of the flute 38 preferably is generally ampullaceous, as shown best in FIG. 2, along substantially the entire length of the elongated body 30.

The hollow envelope 32 defines an open end 50 and a fluid exit port 52. Envelope 32 is removably mounted at the open end thereof to the head portion 34 of the elongated body 30. The hollow envelope 32 is dimensioned to surround the tip 16 and its lateral reflector 24, and is in fluid flow communication with the longitudinal flute 38 through the open end 50. The fluid exit port 52 enables a cooling liquid to pass through envelope 32 during irrigation.

Preferably, the hollow envelope 32 also includes a mounting collar 54 for removable engagement with the head portion 34 of the elongated body 30, as best shown in FIG. 3. The mounting collar 54 may be removably engageable with the head portion 34 by any suitable means, such as, for example, friction fit, snap fit, thread engagement, or the like. As shown in FIGS. 3 and 6, for example, an externally

4 threaded extension 55 may extend from the head portion 34 of the elongated body for engagement with internal threads 56 provided in the mounting collar 54. An "O" ring (not shown), for example, of a silicone or like material may be utilized to format rotation of the hollow envelope after it is screwed or snapped onto the elongated body 30. While the mounting collar 54 may be constructed of any suitable material, such as, for example, metal, plastic, or ceramic, a metal mounting collar is preferred. It may be permanently secured to the hollow envelope 32 in any suitable manner, such as a friction fit or an adhesive.

Means are also included for holding and immobilizing the mounting stem 22 within the elongated body 30. In the preferred embodiment, a coil spring 60 is seated within a circumferential groove 62 that is defined on the inner side of the head portion 34 of the elongated body 30 so that the spring extends partially or entirely around the cylindrical bore 40, as shown best in FIG. 3. When the heat sink segment 23 of mounting stem 22 is disposed within the flute 38, the spring 60 exerts an immobilizing force on the heat sink segment 23 of mounting stem 22 as heat sink segment 23 is nested within flute 38.

It is appreciated, however, that the mounting stem 22 may be immobilized within the elongated body 30 in any other suitable manner. For example, instead of (or in addition to) the coil spring 60, the flute 38 and the mounting stem 22 may be sized or configured in a manner such that the head portion 34 exerts an immobilizing force on the mounting stem.

The hollow envelope 32 may be transparent, translucent or opaque, in whole or in part, and may be constructed of any suitable material. It may be constructed in whole or in part of quartz, or, if desired, ceramic for increased effectiveness during ablation procedures. The hollow envelope 32 may also be sandblasted or coated to provide in whole or in part a translucent region or an opaque region. The hollow envelope 32 may, for example, be constructed of quartz, fused silica, synthetic sapphire, a heat-resistant polymeric material such as polycarbonate, and frosted by sand blasting for example, in whole or in part, which creates cavities in which tissue and blood can lodge and absorb heat, or it may be coated in whole or in part with a ceramic material such as, for example, alumina, zirconia, a zirconia/alumina mixture, an alumina/titania mixture, or any other suitable ceramic material. Preferably, the ceramic coating on the hollow envelope 32 has a thermal conductivity less than that of live mammalian tissue for increased effectiveness.

The hollow envelopes 32 illustrated in FIGS. 4-8, for example, are shown entirely transparent or translucent. The hollow envelope 32 illustrated in FIG. 9 is constructed of a transparent or translucent material but is coated with an opaque material (or, alternatively, constructed partially of a transparent or translucent material and partially of an opaque material). The hollow envelope 32 of FIG. 10 is coated entirely with (or, alternatively, constructed entirely of) an opaque material.

As shown in FIG. 8, if desired, the hollow envelope 32 may comprise a lateral cutting edge 33 which can be used to cut tissue during medical procedures. The cutting edge may be positioned directly above the reflective cavity 18, or at any other desired location.

In one embodiment, the heat sink segment 23 of mounting stem 22 has a cross section which may be an elongated triangle or finned bore 40 of flute 38 may have a complementary cross section, so that the tail portion 36 of elongated body 30 can engagingly fit over the heat sink segment 23 of mounting stem 22 in only one position.

If the elongated groove 42 of elongated body 30 is disposed facing the reflective cavity 18 of lateral lasing device 12, when bore 40 of flute 38 is engagingly disposed over heat sink segment 23 of mounting stem 22, fluid introduced into the urethra through the endoscope will flow through groove 42 into hollow envelope 32 and over reflective cavity 18 and lateral reflector 24, providing both cleaning and cooling thereto.

In a preferred embodiment, flute 38 is oriented so that, when bore 40 is engagingly disposed over heat sink segment 23 of mounting stem 22, longitudinal groove 42 is disposed on the side of lateral lasing device 12 opposite the reflective cavity 18, and fluid flow mainly occurs along and cools the side of lateral lasing device 12 opposite that of reflective cavity 18.

While it may be economically feasible to attach one attachable or exchangeable enclosure 10, which is transparent to the wavelength of light being used, for coagulation of tissue lateral to the axis of the optical fiber of the lateral lasing device 12, remove said device, and attach another attachable enclosure 10, whose entire exterior has been coated with a light absorbing substance or frosted, forming cavities in which tissue can lodge and absorb heat, for ablation of tissue lateral to the axis of the optical fiber of lateral lasing device 12, it would be economically desirable to use one attachable enclosure 10 to accomplish both effective coagulation and ablation.

In the preferred embodiment, the hollow enclosure is made of quartz, one hemisphere of which is coated with a light absorbing substance such as carbon, and the other hemisphere is clear and transparent to wavelengths of light such as from 400 nanometers to 2400 nanometers, the quartz being of low hydroxyl content when wavelengths of 1900 to 2400 nanometers are utilized.

The light absorbing coated hemisphere enables the lateral lasing device to emit light directly into the portion of the carbon coated hemisphere which can be brought into contact or near contact with tissue to effectively ablate the same, whereas in conventional contact types, such as manufactured by Surgical Lasers Technologies, Inc. of Malvern, Pa., light is emitted from an optical fiber directly ahead, into a synthetic sapphire of quartz tip mounted opposite the distal end of the optical fiber. Typically, the entire distal face of the quartz or sapphire tip is coated with a heat radiating, light absorbing substance and heated by the light energy emitted from the optical fiber. However, only a portion of the heated contact tip can be brought into contact with prostatic or other tissue lying laterally from the axis of the optical fiber, and the balance of the energy is dissipated into the surrounding fluid medium.

While mounting collar 54 of hollow envelope 32 and head portion 34 of elongated body 30 can each have screw threads, with an "O" ring to enable the hollow envelope 32 to be rotated about head portion 34 of elongated body 34, when the two are engaged, mounting collar 54 and head portion 34 can each have a means for attachment to each other by friction or a snap mechanism, movement of envelope 32 may occur during use. Thus, it would be preferable to enable collar 54 of hollow envelope 32 to be engagingly attached to head portion 34 of elongated body 30 in only two positions—one in which the transparent hemisphere is directly over reflective cavity 18 and lateral reflector 24, and the other in which the hemisphere of hollow envelope 32 which has been coated with a light absorbing substance or frosted is disposed directly over reflective cavity 18 and lateral reflector 24. This may be accomplished by a luer lock type mechanism, a BNC interlock, or the like.

Alternatively, extension 55 of head portion 34 can have a cross section consisting of a circle with two, opposite quadrants flattened, at 90° and 180°, i.e. three and nine o'clock, and mounting collar 54 of hollow envelope 32 can have a similar cross section, so the two can be engagingly attached by a snap mechanism, friction fit or other means, in only two positions—one for coagulation and one for ablation.

By disposition of the flat sides of the otherwise cylindrical extension 55 of head portion 34 at 3 and 9 o'clock, flute 38 may communicate with the circular portion of the cross section of mounting collar 54 to enable fluid to pass therethrough and over lateral lasing device 12, in the desired orientation.

If desired, an irrigation tube 64 for supplying a cooling liquid to the lateral reflector 24 may be concentrically mounted on the tail portion 36 by friction or any other suitable means (see FIG. 3). A plurality of ridges 65 may be defined in the tail portion 36 for securing the irrigation tube 64 to the tail portion 36. The irrigation tube 64 is in fluid flow communication with the flute 38 and the hollow envelope 32. The irrigation tube may be constructed of any suitable material such as plastic (e.g., biocompatible polyurethane) or rubber.

If desired, indicia that is visible through an endoscope may be included on the elongated body 30 for indicating to the surgeon the direction of the laser beam. FIG. 4, for example, shows a pair of dots 66 provided on the tail portion 36 of the elongated body 30 and the mounting collar 54. Alternatively, FIGS. 6–10 show two pairs of dots 66 provided on the tail portion 36 of the elongated body and the mounting collar 54. When the elongated body 30 and hollow envelope 32 are properly mounted together, the dots will be aligned and adjacent to one another without a substantial space therebetween. FIG. 5 shows a line 68 on the mounting collar 54 which enables the surgeon to determine the direction of the laser beam.

The mounting collar may also include a peripheral pawl-and-ratchet arrangement that permits a partially coated envelope to be rotated about its axis so as to place a region of different transmissivity in the path of the laser beam emitted by the lasing device.

The mounting stem 22 may be secured to the fiber optic 14 in any suitable manner. The mounting stem of FIGS. 6–10, for example, is crimped around the fiber optic, as illustrated by the crimp marks 70.

The foregoing description is for purposes of illustration only and is not intended to limit the scope of protection accorded this invention. Still other variations and rearrangements of parts are possible and will readily present themselves to those skilled in the art.

What is claimed is:

1. An attachable enclosure for a lateral lasing device which device includes a fiber optic with a distal end adapted for emitting a laser beam and an exposed lateral reflector for the laser beam opposite the distal end of the fiber optic and connected thereto by an elongated mounting stem, the enclosure comprising:

an elongated body having a head portion and a tail portion, the elongated body defining a longitudinal flute for receiving the mounting stem within the body;

means for immobilizing the mounting stem when it is received within the elongated body;

the immobilizing means having a spring disposed between the elongated body and the mounting stem when the mounting stem is received within the elongated body, the spring applying an immobilizing pressure to the mounting stem; and a hollow envelope, having an open end and a fluid exit port, removably mounted to the head portion at its open end, the hollow envelope being dimensioned to surround the lateral reflector and being in fluid flow communication with the longitudinal flute through the open end of the elongated body.

2. The attachable enclosure of claim 1, wherein a circumferential groove is formed on an inner side of the elongated body and the spring is seated within the groove.

3. The attachable enclosure of claim 2 wherein the mounting stem comprises an enlarged diameter segment that defines a heat sink, the spring being disposed about the heat sink when the mounting stem is received within the elongated body.

4. The attachable enclosure of claim 1 wherein the hollow envelope includes a mounting collar for removable engagement with the head portion of the elongated body.

5. The attachable enclosure of claim 4 wherein the mounting collar of the hollow envelope is engageable with the head portion of the elongated body by a friction fit.

6. The attachable enclosure of claim 4 wherein the mounting collar of the hollow envelope is threadingly engageable with the head portion of the elongated body.

7. The attachable enclosure of claim 4 wherein a threaded extension extends from the head portion of the elongated body, the threaded extension being threadingly engageable with the mounting collar of the hollow envelope.

8. The attachable enclosure of claim 4 wherein the attachable enclosure is provided with indicia visible through an endoscope for indicating proper alignment of the hollow envelope and the elongated body.

9. The attachable enclosure of claim 8, wherein the indicia is provided on the tail portion of the elongated body and the hollow envelope.

10. The attachable enclosure of claim 9, wherein the indicia comprises a first dot provided on the tail portion and a second dot provided on the mounting collar, the dots being aligned when the elongated body and hollow envelope are mounted together.

11. The attachable enclosure of claim 4, wherein the elongated body is provided with indicia visible through an endoscope for indicating the direction of the laser beam emitted from the fiber optic.

12. The attachable enclosure of claim 11, wherein the indicia is a line provided on the mounting collar.

13. The attachable enclosure of claim 1 wherein the hollow envelope comprises a ceramic tip and a mounting collar integral with the ceramic tip and complementary to the head portion of the elongated body for removable engagement therewith.

14. The attachable enclosure of claim 1 wherein the hollow envelope comprises a quartz tip and a mounting collar integral with the quartz tip and complementary to the head portion of the elongated body for removable engagement therewith.

15. The attachable enclosure of claim 1, wherein the hollow envelope has a ceramic coating on at least a portion of its extension.

16. The attachable enclosure of claim 15 wherein the ceramic is alumina.

17. The attachable enclosure of claim 15, wherein the ceramic is zirconia.

18. The attachable enclosure of claim 15, wherein the ceramic is a zirconia/alumina mixture.

19. The attachable enclosure of claim 1, wherein the hollow envelope has a coating having a thermal conductivity less than that of live mammalian tissue.

20. The attachable enclosure of claim 1, wherein at least a portion of the envelope is frosted.

21. The attachable enclosure of claim 1, wherein the envelope is transparent and at least a portion of the envelope is provided with an opaque coating.

22. The attachable enclosure of claim 1, wherein the envelope is transparent and at least a portion of the envelope is provided with a translucent coating.

23. The attachable enclosure of claim 1, wherein the envelope is frosted and at least a portion of the envelope is provided with an opaque coating.

24. The attachable enclosure of claim 1 wherein the envelope is opaque.

25. The attachable enclosure of claim 1, further comprising an irrigation tube mounted at distal end thereof to the elongated body for conveying a cooling liquid into the interior of the hollow envelope.

26. The attachable enclosure of claim 25, wherein the irrigation tube is in fluid flow communication with the flute and the hollow envelope.

27. The attachable enclosure of claim 26, wherein the irrigation tube is mounted on the tail portion of the elongated body.

28. The attachable enclosure of claim 27, wherein a plurality of ridges are defined on the tail portion of the elongated body for securing the irrigation tube thereto.

29. The attachable enclosure of claim 1, wherein an flute has a generally ampullaceous transverse cross section along substantially the entire length of the flute.

30. The attachable enclosure of claim 1, wherein an flute is defined by a circular bore and longitudinal groove that intersect and extend along the entire length of the elongated body.

31. An attachable enclosure for a lateral lasing device which device includes a fiber optic with a distal end adapted for emitting a laser beam and an exposed lateral reflector for the laser beam opposite the distal end of the fiber optic and connected thereto by an elongated mounting stem, the enclosure comprising:

an elongated body having a head portion and a tail portion, the elongated body defining a longitudinal flute for receiving the mounting stem within the body;

means for immobilizing the mounting stem when it is received within the elongated body; and a hollow envelope, having a cutting edge, an open end, and a fluid exit port removably mounted to the head portion at its open end, the hollow envelope being dimensioned to surround the lateral reflector and being in fluid flow communication with the longitudinal flute through the open end of the elongated body.

32. The attachable enclosure of claim 31 wherein the cutting edge extends along a longitudinal axis of the envelope.

* * * * *

UNITED STATES PATENT AND TRADEMARK OFFICE
CERTIFICATE OF CORRECTION

PATENT NO. : 5,746,737
DATED : May 5, 1998
INVENTOR(S) : Vahid Saadat

It is certified that error appears in the above-indentified patent and that said Letters Patent is hereby corrected as shown below:

Col. 3, line 3, "i:ail" should be -- tail --.
Col. 8, line 34, "an" should be -- the --.
Col. 8, line 36, "the" (first occurrence) should be -- an --.
Col. 8, line 37, "an" should be -- the --.
Col. 8, line 39, "the" (first occurrence) should be -- an --.

Signed and Sealed this

Fourth Day of August, 1998

Attest:

BRUCE LEHMAN

Attesting Officer

Commissioner of Patents and Trademarks